United States Patent [19]

Cramer et al.

[11] 4,096,857

[45] Jun. 27, 1978

[54] TELESCOPICALLY ADJUSTABLE SURGICAL INSTRUMENT

[75] Inventors: Rudolf Cramer, Piesenkam; Jüergen J. Hildebrandt, Brunnthal, both of Germany

[73] Assignee: Messerschmitt-Boelkow-Blohm GmbH, Munich, Germany

[21] Appl. No.: 754,127

[22] Filed: Dec. 27, 1976

[30] Foreign Application Priority Data

Jan. 20, 1976 Germany .............................. 2601938

[51] Int. Cl.$^2$ .......................... A61F 5/04; A61B 17/18
[52] U.S. Cl. ................ 128/84 R; 128/92 R; 128/92 D
[58] Field of Search ............... 128/84 R, 84 B, 84 C, 128/92 D, 92 R, 92 B, 92 BA, 92 E, 83

[56] References Cited

U.S. PATENT DOCUMENTS

| 3,528,085 | 9/1970 | Reynolds | 128/92 D |
| 3,604,414 | 9/1971 | Borges | 128/92 D |
| 3,900,025 | 8/1975 | Barnes | 128/84 R X |
| 3,976,060 | 8/1976 | Hildebrandt et al. | 128/92 R X |

FOREIGN PATENT DOCUMENTS

| 867,422 | 2/1953 | Germany | 128/92 D |
| 2,213,283 | 8/1973 | Germany | 128/92 D |
| 373,516 | 1/1964 | Switzerland | 128/92 D |
| 335,797 | 3/1959 | Switzerland | 128/92 D |

*Primary Examiner*—Ronald L. Frinks
*Attorney, Agent, or Firm*—W. G. Fasse; W. W. Roberts

[57] ABSTRACT

A telescopically adjustable surgical instrument for a distraction apparatus used in performing an elongation osteotomy comprises a rigid support rail having a guide chamber or guide recess and a rigid extension rail axially slidable in said recess. The extension rail has hinged bone connecting plates by means of which the extension rail may be attached to the distal part of a bone. An extension drive mechanism may be releasably connected to the two rails. The instrument is completely implantable. After the distraction, the position of the extension rail is fixed and the drive mechanism may be easily removed.

6 Claims, 6 Drawing Figures

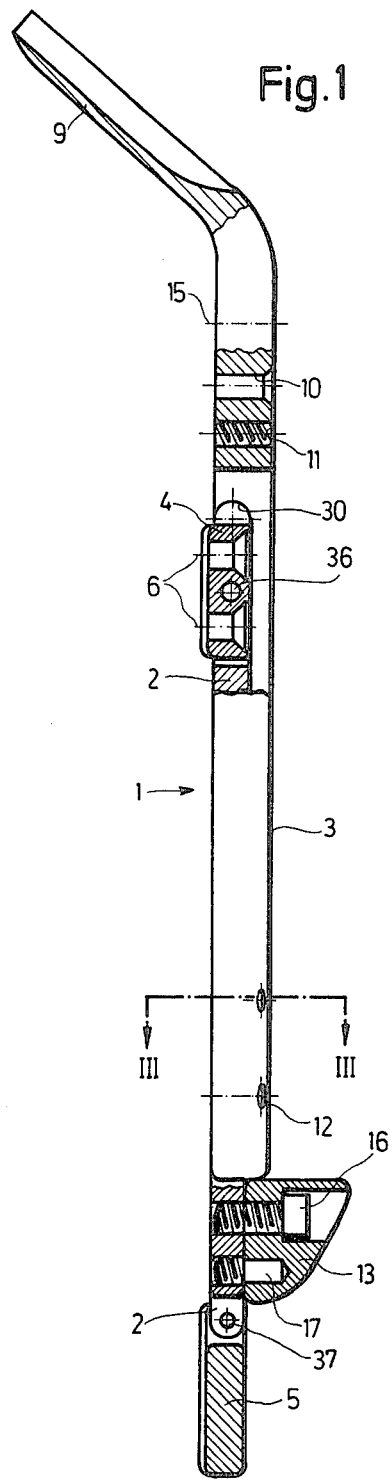
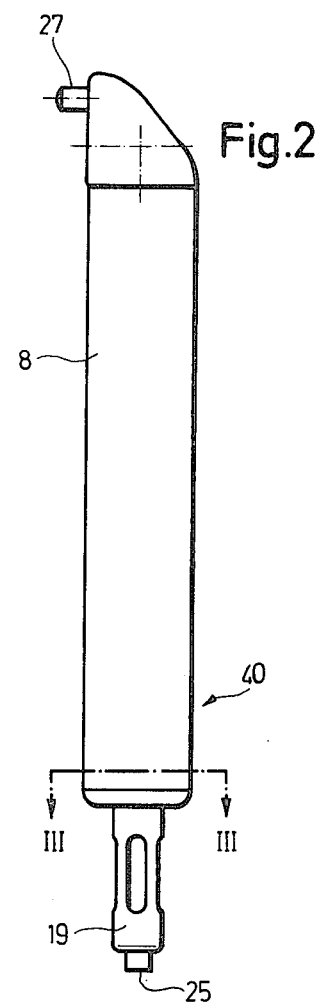
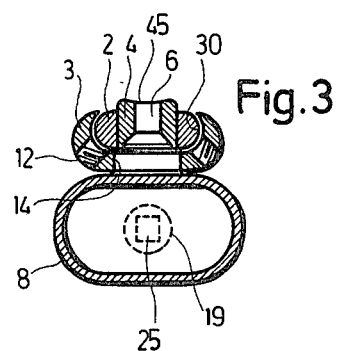

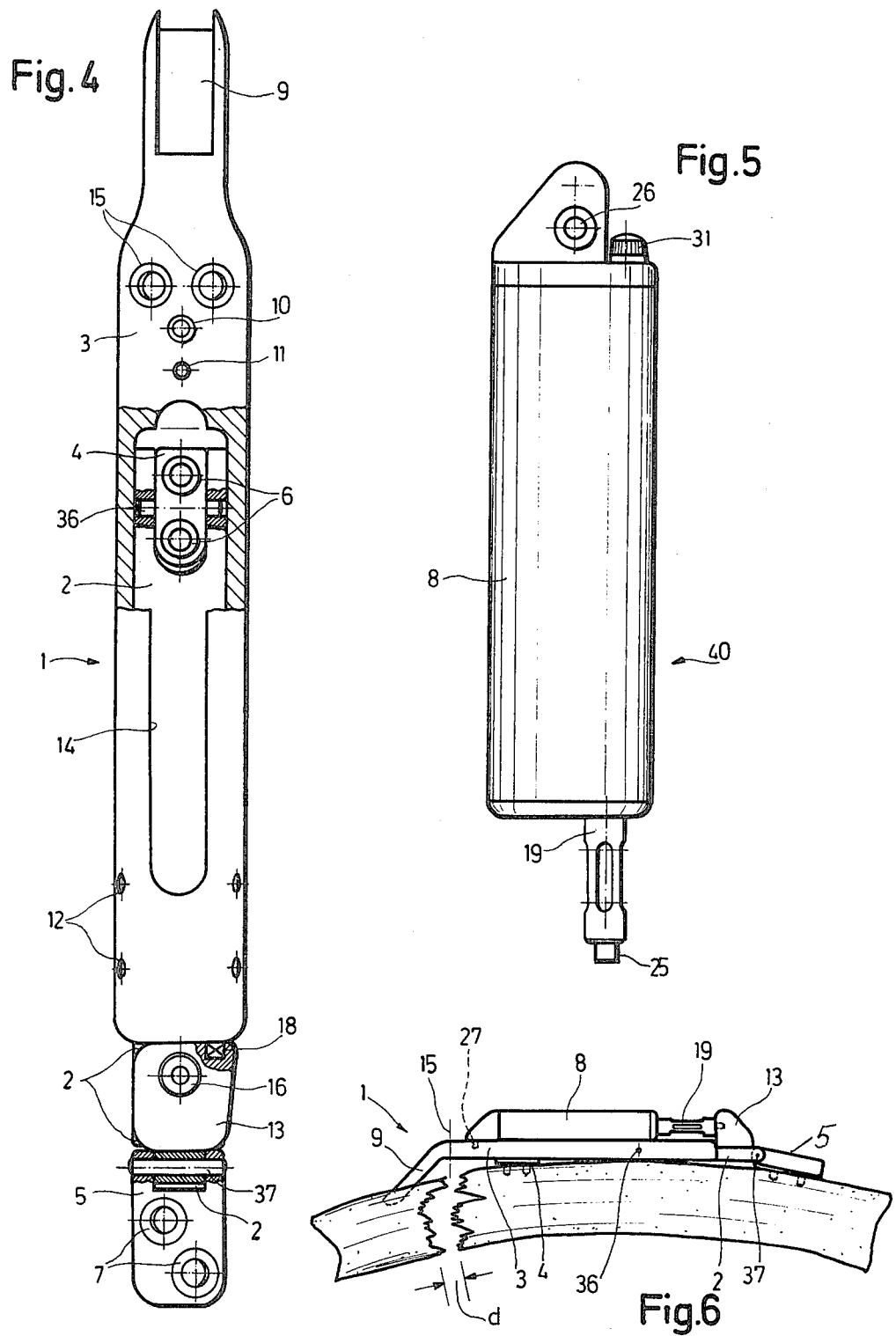

TELESCOPICALLY ADJUSTABLE SURGICAL INSTRUMENT

BACKGROUND OF THE INVENTION

The invention relates to a telescopically adjustable surgical instrument for a distraction apparatus used in performing an elongation osteotomy.

Surgeons have used such instruments in order to avoid tissue damage during an elongation osteotomy. Such instruments include two telescopically adjustable rails for gradually increasing the spacing between the severed ends of a bone. An elongation osteotomy is performed to gradually increase the length or correct the deformity of a bone, while simultaneously elongating the tissue. Once the distraction or the elongation is completed, the rails maintain the final position of the bone parts. Thus, the desired lengthening of the bone is achieved without damaging the soft tissue around the bone.

Distraction devices have been proposed which reduce the danger of infection and lower the flexural or bending moments arising in the rails and the bone parts to which the rails are attached. These flexural moments occur between the anchoring points where the rails are secured to the bone. To minimize these flexural moments the rails are implanted close to the bone. Such rails may be telescopically adjusted externally by a tool as disclosed, for example, in German DAS No. 22 13 283. It is also known to adjust the rails by implanted drive means, as disclosed in U.S. Pat. No. 3,976,060.

Previously known distraction devices have in addition to flexural weaknesses, the disadvantage that an optimal adaptation of the rails to the shape of the bone is not possible in all elongation osteotomies. The various curvatures of a bone, such as a femur, prevent an optimal adaptation in most instances. Another disadvantage of the prior art devices is that the entire distraction apparatus, i.e., the combination of guide rail, extension rail and drive means must remain in the patient until the condition of the bone is stabilized even though the extension has already been executed. However, after the extension is accomplished the bone parts need only be fixed or locked in the extended position. Yet in the prior art arrangements, the drive means after having served its purpose remains connected to the distraction device, thereby hindering or interfering with the further treatment and healing process.

OBJECTS OF THE INVENTION

In view of the foregoing, it is the aim of the invention to achieve the following objects, singly or in combination:

to provide a telescopically adjustable guide rail and extension rail for a distraction apparatus suitable for an optimal adaptation to a bone of any shape in all elongation osteotomic surgery applications;

to provide a drive assembly for an extension drive mechanism such that the assembly may be easily connected to and disconnected from the distraction device, thereby avoiding the disadvantages of the prior art;

to provide a distraction device to which an anchoring means may be easily connected to aid the surgeon in proximally anchoring a blade in the bone which is to be lengthened; and to provide a distraction device and drive assembly which are completely implantable although easily separable from each other, thereby reducing the danger of infection and greatly helping the healing process.

SUMMARY OF THE INVENTION

According to the invention there is provided a telescopically adjustable distraction device for an osteotomic operation suitable for optimal adaptation to the given shape of any bone in all elongation osteotomies. The device is constructed so that a drive mechanism may be releasably connected to the two rails. After the drive mechanism has served its purpose, the drive assembly is easily removed without any force application to the bone.

The device of the invention comprises a support guide rail having an axial chamber or recess and an extension rail slidable in the chamber. Both rails are rigid against bending moments. The extension rail slides within the chamber of the support rail until the distraction is completed. The support rail includes an arrangement which rigidly secures the final position of the extension rail relative to the guide rail. Connecting plates are journaled or hinged to each end of the slidable rail. These plates have holes through which fastening screws attach the extension rail to the distal part of a bone, such as a femur. Fastening means anchor the support guide rail to the proximal part of the femur.

A hole and an adjacent tapped hole are located below the blade means in a shaft of the support guide rail. A drive device may be connected to the guide rail in the shaft region thereby using these holes as mounting holes. A detachable support block for the drive means is secured to the extension rail. Said anchoring or bone connecting means may include a curved blade means for making an initial anchoring penetration into the proximal part of the femur. The above mentioned anchoring holes for a drive means may be advantageously used for insertion of an auxiliary tool for making said penetration. The auxiliary tool is then removed. Said support block for positioning the drive means is releasably connected to that part of the extension rail which extends out of the support rail. A drive assembly or extension drive mechanism is attached to the support rail utilizing the anchoring hole and tapped hole in which the auxiliary tool was inserted. A driving rod extends out of the drive assembly and engages a recess in the positioning block of the extension rail. Actuating the drive mechanism, which may be by remote control, moves the extension rail gradually partially out of the support rail. This action separates the proximal and distal parts of the femur. Clamping or set screws fix the desired position of the extension rail through tapped holes in the support rail after the distraction is completed. The drive assembly and positioning or support block may then be easily disconnected. The absence of the extension drive means facilitates the completion of the elongation osteotomy.

BRIEF FIGURE DESCRIPTION

In order that the invention may be clearly understood, it will now be described, by way of example, with reference to the accompanying drawings, wherein:

FIG. 1 shows a side view, in partial section, of a distraction device of the invention comprising a slidable extension rail and a support guide rail;

FIG. 2 shows a side view of a drive assembly which may be detachably secured to the distraction device proper;

FIG. 3 is a section along line III—III in FIG. 1 and FIG. 2 showing the connection of the drive assembly of FIG. 2 to the device of FIG. 1 with the extension rail in the fully extended position;

FIG. 4 shows a front view, in partial section, of the guide conductor 1 of FIG. 1;

FIG. 5 shows a front view of the housing assembly of FIG. 2 with a partially broken away front portion; and FIG. 6 shows a simplified side elevation of the present device with the extension rail in a fully extended position and secured to a femur.

DETAILED DESCRIPTION OF PREFERRED EXAMPLE EMBODIMENTS:

According to the invention, as shown in FIG. 1, a distraction device 1 comprises a support guide rail 3 and a slidable extension rail 2. A curved blade 9 forms part of a shaft or first end of the support rail 3. A surgeon applies a force along the longitudinal axis and drives it into a bone which is to be lengthened, such as a femur, preferably into the proximal end of a bone. This force causes the blade to penetrate the bone to anchor it to the femur. As seen in FIG. 1, a hole 10 and a tapped or threaded hole 11 are located in the shaft of the support rail 3 adjacent to the first end. A tool not shown may be readily attached to or inserted into the device near the blade 9 by means of suitable fasteners through the holes 10 and 11.

The surgeon smoothly guides the blade 9 into the femur by using an auxiliary tool for applying a force which is directed in parallel to the longitudinal axis of the blade 9. After the blade 9 penetrates the bone and is anchored therein, the auxiliary tool is removed. In addition to the just described anchoring, fastening screws aid in proximally securing the rigid support and guide rail 3 to the femur, said screws extending through the holes 15, shown in FIGS. 1 and 4. As best seen in FIGS. 1 and 3, the rigid extension rail 2 slides axially inside a tubular chamber or recess 30 formed in the support rail 3. The tubular chamber 30 extends longitudinally from a second end toward a first end in the support rail 3 to a point adjoining the shaft thereof. The rails 2 and 3 are made of flexurally rigid material, for example stainless steel. At the second or lower end of the support rail 3, the tubular chamber 30 forms an opening. The extension rail 2 extends out of the opening, as shown in FIGS. 1 and 4.

As shown in FIG. 4, a journal pin 36 hingedly connects an adapting connecting plate 4 to the upper or inner end of the extension rail 2. A journal pin 37 hingedly connects an adapting, connecting plate 5 to the lower or outer end of the extension rail 2. The holes 6 and 7 penetrate the connecting plates 4 and 5, respectively, as shown in FIGS. 1 and 4. The hollow chamber 30 comprises a longitudinal access slot 14 shown in FIGS. 3 and 4. Fastening screws, not shown, attach the plate 4 of the rail 2 to the distal part of the femur through the drill holes 6 via the access slot 14. Further fastening screws, not shown, attach the plate 5 of the rail 2 to a further distal part of the femur. According to FIG. 3, the connecting plate 4 comprises a cross sectionally arcuate groove 45 to match the curvature of the femur. The connecting plate 5 has a similar shape. The hinge or joint type construction of the connecting plates 4 and 5 provides an optimal adaptation of the distractor 1 to the femur, especially in combination with bent blade 9. Such an arrangement minimizes any gaps between the distraction device 1 and the femur. A good fit always results regardless what curvatures the femur may have. The excellent contact achieved between the distraction device 1 and the femur eliminates stresses or flexural moments, which might otherwise occur. The optimal adaptation avoids any tensile loads on the attachment screws, such as in the holes 7 or 15. Another advantage is seen in that any spacing between a bone and the device is minimized.

FIGS. 2 and 5 show a drive assembly 40 provided for a remote controllable, drive mechanism not shown in detail.

As one example, the drive mechanism may have a micrometer type action. In this case, turning a knob 31 gradually advances a driving rod 19. The drive assembly 40 comprises a housing 8 and a driving rod 19. The drive assembly 40 is made of material which is body compatible. Thus, the drive assembly is fully implantable. The driving rod 19 extends out of the housing 8. A positioning or support block 13 is mounted on the lower or outer end of the extension rail 2 in an easily removable manner, as shown in FIGS. 1 and 4. A screw 16 and a centering pin 17 connect the positioning block 13 to the rail 2. The positioning block 13 has a tetragonal recess or otherwise shaped cavity 18, with the open end facing upwardly. An end formation 25 of the driving rod 19, shown in FIG. 2, has a corresponding shape which fits into the recess 18. After the distraction device 1 has been attached to the femur in the above described form-fitting manner, the drive assembly 40 is connected to the support rail 3. The end formation 25 of the driving rod 19 is inserted into the recess 18 of the positioning block 13. A fastening screw pin 27, shown in FIG. 2 and a fastening screw not shown, connect the upper end of the housing 8 to the shaft of the support rail 3, through the holes 10 and 11, respectively.

After the drive housing 8 has been connected to the distractor 1, the surgeon cuts through the femur as shown at "d" in FIG. 6. The drive mechanism in the housing 8 actuates the driving rod 19 which gradually moves the positioning block 13, whereby the extension rail 2 slides within the chamber 30 of the support rail 3, and the attached plates 4 and 5 pull the distal part away from the proximal part. This action causes the desired separation between the proximal and distal parts of the femur.

Performing the extension as described above accomplishes the desired lengthening of the leg with only a gradual stretching of the tissue. The final position of the extension rail 2 relative to the guide rail 3 fixed by clamping screws, not shown, but extending through the threaded holes 12 shown in FIGS. 1, 3, and 4. After the final position of the proximal and distal parts of the femur is established, the drive assembly 40 and the positioning block 13 may be easily removed without applying any forces to the bone. The distractor 1 remains in the body of the patient until the final interconnection of the bone. An important advantage of the invention is that the patient is subjected to significantly less stress than compared with prior art arrangements. In addition, the implantability of the distractor 1 and the drive assembly 40 considerably reduces any danger of infection.

Although the invention has been described with reference to specific example embodiments, it is to be understood, that it is intended to cover all modifications and equivalents within the scope of the appended claims.

What is claimed is:

1. A telescopically adjustable surgical instrument, especially for performing an elongation osteotomy, comprising rigid guide rail means including a first end and a second end, recess means in said guide rail means extending from said second end toward said first end, rigid extension rail means having an inner end and an outer end, said inner end being received for axial movement in said recess means of said guide rail means, first bone connecting means forming part of said first end of said rigid guide rail means, second bone connecting means operatively secured to said rigid extension rail means, first extension actuator support means operatively connected with said rigid guide rail means, second actuator support means operatively connected to said rigid extension rail means, and connector means for rigidly but releasably securing said guide rail means and said extension rail means to each other, said first extension actuator support means comprising connecting means located in said rigid guide rail means substantially adjacent to said first end, wherein said second actuator support means comprise support block means releasably secured to said rigid extension rail means substantially at the outer end thereof, and wherein said connector means comprise set screw means.

2. The instrument of claim 1, wherein said first bone connecting means comprise a bent blade type member forming an integral part of said first end of said rigid guide rail means.

3. The instrument of claim 1, wherein said recess means in said rigid guide rail means include access means for said second bone connecting means, said access means being operatively positioned so that said second bone connecting means are accessible through said access means in any position of said rigid extension rail means within said recess means.

4. The instrument of claim 1, wherein said rigid guide rail means includes threaded holes in its second end for receiving said set screw means.

5. The instrument of claim 1, wherein said rigid guide rail means include a closed end slot extending parallel to said recess means, said slot having a length corresponding to the extension length of said instrument.

6. A telescopically adjustable surgical instrument, especially for performing an elongation osteotomy, comprising rigid guide rail means including a first end and a second end, recess means in said guide rail means extending from said second end toward said first end, rigid extension rail means having an inner end and an outer end, said inner end being received for axial movement in said recess means of said guide rail means, first bone connecting means forming part of said first end of said rigid guide rail means, second bone connecting means operatively secured to said rigid extension rail means, first extension actuator support means operatively connected with said rigid guide rail means, second actuator support means operatively connected to said rigid extension rail means, and connector means for rigidly but releasably securing said guide rail means and said extension rail means to each other, said second bone connecting means comprising a first bone connector plate hinged to said inner end of said rigid extension rail means in said recess means which is accessible from the outside of said rigid guide rail means and second bone connector plate means hinged to the outer end of said rigid extension rail means.

* * * * *